United States Patent
Morganstern et al.

(10) Patent No.: US 10,426,835 B2
(45) Date of Patent: *Oct. 1, 2019

(54) METHOD FOR TREATING PEYRONIE'S DISEASE

(71) Applicant: BMR Medical LLC, Marietta, GA (US)

(72) Inventors: Steven Morganstern, Sandy Springs, GA (US); Carlos Becerra, Atlanta, GA (US)

(73) Assignee: BMR Medical LLC, Marietta, GA (US)

( * ) Notice: Subject to any disclaimer, the term of this patent is extended or adjusted under 35 U.S.C. 154(b) by 577 days.

This patent is subject to a terminal disclaimer.

(21) Appl. No.: 15/132,418

(22) Filed: Apr. 19, 2016

(65) Prior Publication Data

US 2017/0296209 A1    Oct. 19, 2017

(51) Int. Cl.
*A61B 17/22* (2006.01)
*A61K 41/00* (2006.01)
(Continued)

(52) U.S. Cl.
CPC .......... *A61K 41/0028* (2013.01); *A61B 8/06* (2013.01); *A61B 8/488* (2013.01);
(Continued)

(58) Field of Classification Search
CPC .. A61K 2300/00; A61K 31/277; A61K 33/00; A61K 41/0028; A61K 47/02;
(Continued)

(56) References Cited

U.S. PATENT DOCUMENTS 5,554,103 A    9/1996 Zheng et al.
5,997,540 A   12/1999 Zheng et al.
(Continued)

FOREIGN PATENT DOCUMENTS

RU    2 256 405    7/2005

OTHER PUBLICATIONS

Anti-Aging Medical Systems: "Carboxy Pen"; believed to have published on Apr. 24, 2013.
(Continued)

*Primary Examiner* — Ruth S Smith
(74) *Attorney, Agent, or Firm* — Barnes & Thornburg LLP; Jeffrey R. Stone

(57) ABSTRACT

In a method of treating a patient having diffuse plaque and/or a plaque mass associated with Peyronie's disease in a penile region, a battery of tests is performed to quantify an initial state of parameters associated with Peyronie's disease in the patient. Low intensity shock wave therapy is applied to the plaque mass in the penile region, thereby softening the plaque mass and disrupting any calcification in the plaque mass. Carbon dioxide is injected into the plaque mass. The battery of tests is repeated to quantify a current state of parameters associated with Peyronie's disease in the patient and the current state is compared to the initial state. The aforementioned treatment steps are repeated until the current state differs from the initial state by at least a predetermined amount.

20 Claims, 4 Drawing Sheets

(51) Int. Cl.
| | |
|---|---|
| *A61B 8/06* | (2006.01) |
| *A61B 8/08* | (2006.01) |
| *A61K 31/277* | (2006.01) |
| *A61K 9/00* | (2006.01) |
| *A61K 47/02* | (2006.01) |
| *A61K 33/00* | (2006.01) |

(52) U.S. Cl.
CPC ...... *A61B 17/22004* (2013.01); *A61K 9/0034* (2013.01); *A61K 31/277* (2013.01); *A61K 33/00* (2013.01); *A61K 47/02* (2013.01)

(58) Field of Classification Search
CPC .. A61K 9/0034; A61B 17/22004; A61B 8/06; A61B 8/488
See application file for complete search history.

(56) References Cited

U.S. PATENT DOCUMENTS

| | | |
|---|---|---|
| 6,251,076 B1 | 6/2001 | Hovland et al. |
| 6,572,621 B1 | 6/2003 | Zheng et al. |
| 6,589,267 B1 | 7/2003 | Hui |
| 6,620,116 B2 | 9/2003 | Lewis |
| 6,858,012 B2 | 2/2005 | Burns et al. |
| 6,863,670 B2 | 3/2005 | Zheng et al. |
| 6,962,599 B2 | 11/2005 | Hui |
| 7,048,702 B2 | 5/2006 | Hui |
| 7,314,478 B2 | 1/2008 | Hui |
| 7,517,312 B2 | 4/2009 | Loeb et al. |
| 7,713,211 B2 | 5/2010 | Anderson et al. |
| 7,981,066 B2 | 7/2011 | Lewis |
| 9,132,245 B2 | 9/2015 | Mantell |
| 2006/0216338 A1* | 9/2006 | Easterling ............ A61K 9/0014 424/449 |
| 2012/0215142 A1 | 8/2012 | Spector et al. |
| 2013/0245541 A1 | 9/2013 | Mantell |
| 2015/0073312 A1 | 3/2015 | Ein-Gal |
| 2017/0258674 A1 | 9/2017 | Morganstern et al. |

OTHER PUBLICATIONS www.bodyrenewal.co.za: "Barboxytherapy for Sexual Rejuvenation / Erectile Dysfunction"; Sep. 9, 2015.
Froschemaier et al.: "Enhanced External Counterpulsation as a New Treatment Modality for Patients with Erectile Dysfunction"; Urologia Internationals; Jul. 20, 1998.
Gruenwald et al: "Shockwave treatment of erectile dysfunction"; https://beta.openaire.eu/search/publication?articleId=od; 2013.
Hind et al.: "Initial results of treatment with Linear Shockwave Therapy (LSWT) by Renova in patients with Erectile Dysfunction"; believed to have been published Aug. 30, 2013.
Fabrizio et al.: "Experience of Carboxytherapy in Conservative Treatment of Peyronie's disease"; XXI Congresso Nazionale Roma, Associazione Urologi Italiani; 2012.
Reisman et al: "Initial experience with linear focused shockwave treatment for erectile dysfunction: a 6-month follow-up pilot study"; International Journal of Impotence Research (2014), 1-5; Oct. 18, 2014.
Stein: "Endothelial Dysfunction, Erectile Dysfunction, and Coronary Heart Disease: The Pathophysiologic and Clinical Linkage"; Reviews in Urology; 2003.
Notification of related application; U.S. Appl. No. 15/064,162, filed by Morganstern et al. filed Mar. 8, 2016 is commonly owned with the present application and may contain related subject matter.

* cited by examiner

METHOD FOR TREATING PEYRONIE'S DISEASE

BACKGROUND OF THE INVENTION

1. Field of the Invention

The present invention relates to treatment methods and, more specifically, to a method of treating Peyronie's disease.

2. Description of the Related Art

Peyronie's disease (also known as induratio penis plastica) is an acquired inflammatory condition of the penis often associated with penile curvature. It is a connective tissue disorder involving the growth of fibrous plaques in the soft tissue of the penis. Scar tissue forms in the tunica albuginea, the thick sheath of tissue surrounding the corpora cavernosa causing pain, abnormal curvature, erectile dysfunction, indentation, loss of girth and shortening. The penile curvature of Peyronie's disease is caused by an inelastic scar, or plaque (which may include calcification), that shortens the involved aspect of the tunica albuginea of the corpora cavernosa during erection.

If left untreated, Peyronie's disease may cause fibrotic, nonexpansile thickening of relatively discrete areas of the corpora tunica, typically resulting in focal bend, pain or other functional or structural abnormalities of the erect penis. Surgery has the disadvantage of being expensive and occasionally resulting in unwanted complications. Several medical treatments have been applied, but results so far have been limited. Surgical treatments have been used to treat Peyronie's disease. Collagenase *clostridium histolyticum* (marketed as Xiaflex), an injectable drug, is the most common medical treatment of Peyronie's disease. It is believed that this works by breaking down the excess collagen in the penis that causes Peyronie's disease. This drug has limited success, it can be quite expensive and has significant unwanted complications.

Therefore, there is a need for a reliable and inexpensive non-surgical treatment for Peyronie's disease.

SUMMARY OF THE INVENTION

The disadvantages of the prior art are overcome by the present invention which, in one aspect, is a method of treating a patient having diffuse plaque and/or a plaque mass associated with Peyronie's disease in a penile region, in which a battery of tests is performed to quantify an initial state of parameters associated with Peyronie's disease in the patient. Low intensity shock wave therapy is applied to the plaque mass in the penile region, thereby softening the plaque mass and disrupting any calcification in the plaque mass. Carbon dioxide is injected into the plaque mass. The battery of tests is repeated to quantify a current state of parameters associated with Peyronie's disease in the patient and the current state is compared to the initial state. The aforementioned treatment steps are repeated until the current state differs from the initial state by at least a predetermined amount.

In another aspect, the invention is a treatment method for a patient having a plaque mass associated with Peyronie's disease in a penile region, in which a battery of tests is performed to quantify an initial state of parameters associated with Peyronie's disease in the patient. Low intensity shock wave therapy is applied to a plaque mass in the penile region for about thirteen treatments over a period of seven to eight weeks, including a two week break period of no low intensity shock wave treatment, thereby softening the plaque and disrupting calcification in the plaque mass. A plurality of doses of about 160 cc of carbon dioxide per dose is injected into the plaque mass for a total of about 960 cc. A counterpulsation treatment is applied approximately twice per week during a period of approximately ten weeks to the patient concurrently with the step of applying low intensity shock wave therapy to further disrupt calcification in the plaque mass. A therapeutically effective dose of Verapamil is injected into a dorsal area of the penis before the step of applying low intensity shock wave therapy to the plaque mass as the calcified plaque dictates. The battery of tests is repeated to quantify a current state of parameters associated with Peyronie's disease in the patient and comparing the current state to the initial state. The aforementioned steps are repeated until the current state differs from the initial state by at least a predetermined amount.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
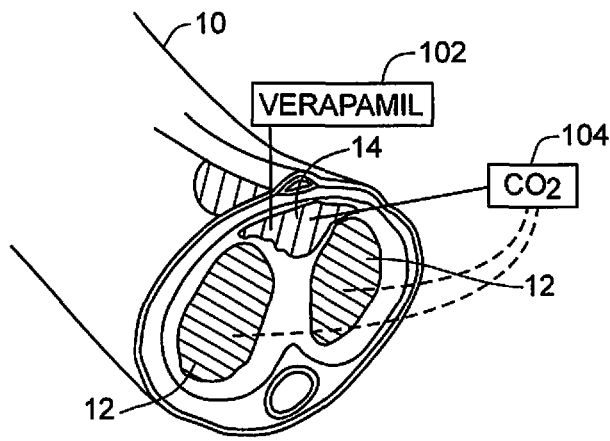
FIG. 1 is a schematic diagram showing treatment of a dorsal plaque.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

As shown in FIG. 1, Peyronie's disease causes curvature of the penis 10 as the result of a plaque mass 14 forming in the dorsal tunica of the penis 10. It can also result from calcification of the corpus cavernosa 12 in the penis 10. As will be shown below, the present treatment protocol includes several steps for improving blood flow through the affected area, along with injecting a therapeutically effective dose of an L-type phenylalkylamine class calcium channel blocker (such as Verapamil) 102 into the plaque mass 14 and also injecting carbon dioxide 104 into the plaque mass 14.

Figure 2:
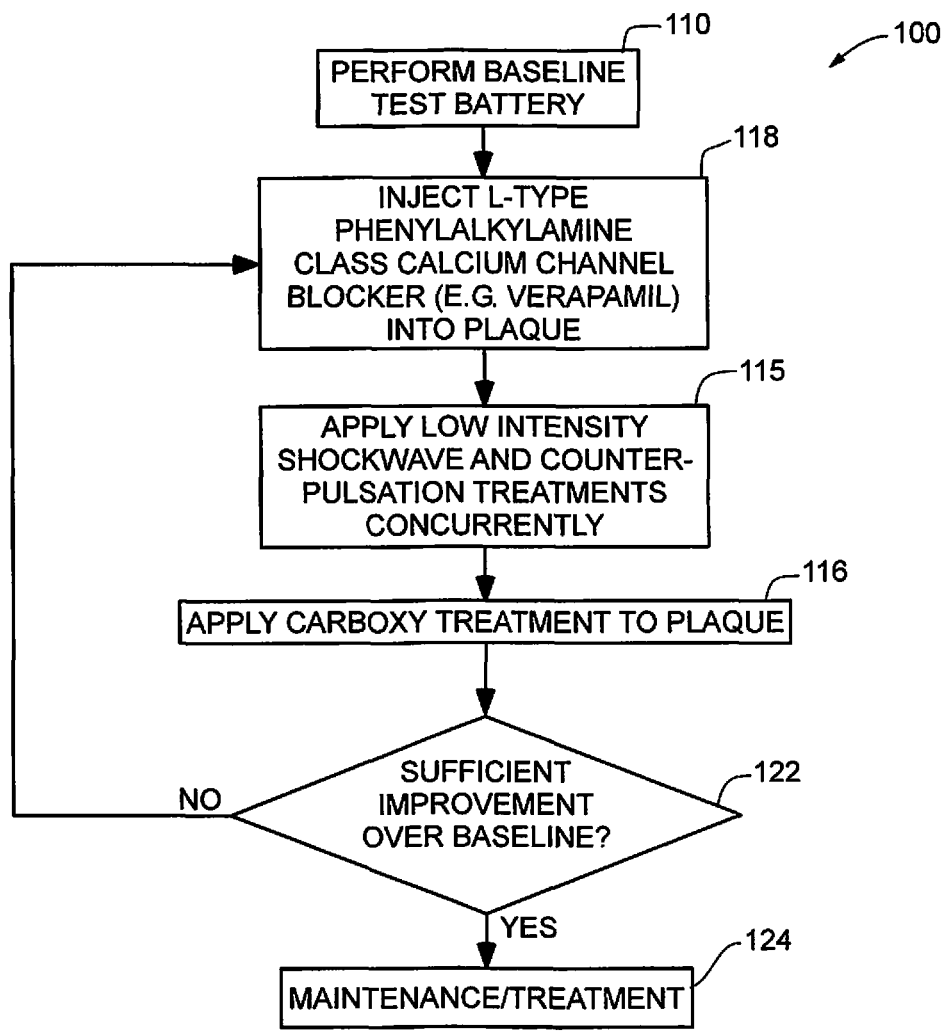
FIG. 2 is a flow chart showing a treatment protocol according to one embodiment of the present invention.

In one embodiment of a treatment protocol 100 for Peyronie's disease, as shown in FIG. 2, comprising performing a baseline test battery 110, injecting an L-type phenylalkylamine class calcium channel blocker, e.g., Verapamil, into the plaque 118, applying low intensity shockwave treatment concurrently with external counter-pulsation treatment, applying carboxy treatment to the plaque 116, then determining if the results of the treatment protocol is sufficient 122 or if the treatment steps beginning with injecting an L-type phenylalkylamine class calcium channel blocker, e.g., Verapamil, into the plaque 118 need to be repeated. If the results are sufficient, then maintenance treatment protocols 124 are followed. Thus, initial test battery is performed on the patient 110 in order to establish a baseline. This test battery typically includes imaging the plaque with an ultrasound imaging device, measuring blood flow in penile blood vessels of the patient with a duplex Doppler ultrasonography blood flow device and measuring pulse wave velocity in a brachial artery and an ankle artery of the patient. Circulatory blood flow velocity in the patient is tested typically with a duplex Doppler. U.S. Pat. No. 6,251,076, issued to Hovland et al., discloses one method of determining blood flow velocity in a penile artery and is incorporated herein by reference for the purpose of disclosing methods of determining blood flow velocity.

Low intensity shock wave therapy is applied to the plaque mass in the penile region 112. This softens the plaque mass and disrupts calcification in the plaque mass. In doing so, low intensity shockwave (LISW) therapy is applied to the plaque mass for about thirteen treatments over a period of seven to eight weeks, including a two week break period of no low intensity shock wave treatment. In the low intensity shockwave treatment (LISW), shock waves having a minimum energy of 0.10 mJmm2 are applied with a local applicator to the penile area once per day for two or three days per week over a course of five weeks. U.S. Publication No. US-2015/0073312-A1, filed by Ein-Gal, discloses one method of low intensity shockwave treatment and is incorporated herein by reference for the purpose of disclosing low intensity shockwave treatment. In a typical treatment, about 300 pulses are applied per minute over the course of between 10 minutes and 20 minutes. The LISW treatment stimulates neovascularization and improves penile blood flow and endothelial function when applied to the corpora cavernosa.

Counter-pulsation treatment is applied twice per week during a period of at least ten weeks 114, which can be done concurrently with the low intensity shock wave therapy. This further disrupts calcification in the plaque mass and improves blood flow. The course of external counter-pulsation treatment includes applying external counter-pulsation treatments to the patient for a predetermined number of days per week for a predetermined number of weeks. In applying the course of external counter-pulsation treatments, an electrocardiogram (ECG) sensing device is applied to the patient and the ECG is sensed. U.S. Pat. Nos. 7,314,478 and 7,314,478, both issued to Hui, disclose a counter-pulsation apparatus and method for controlling the apparatus and is incorporated herein by reference for the purpose of disclosing counter-pulsation methods. An inflatable cuff is applied to at least one of the patient's calf, lower thigh, upper thigh or buttocks. Typically, cuffs are applied to both of the lower thighs and to both of the upper thighs. Counter-pulsations are applied to the cuffs by inflating the cuffs to a pressure of about 300 mm Hg or 6 PSI during a diastole sensed by the ECG. Pressure is then rapidly released from the cuffs during onset of the systole, as sensed by the ECG. Counter-pulsations are performed repeatedly during a treatment sessions that last about one hour, which are performed twice per week over a course of ten weeks. (It should be noted that the term "ECP" is sometimes confused with "EECP," which is a registered a trademark for a brand of ECP. However, the EECP brand can be employed as the type of ECP used.

Carbon dioxide is then injected into the plaque mass 116, which is referred to as "carboxy therapy." In this step, about 960 cc of carbon dioxide is injected into one or both of the corpus cavernosum, the dorsal tunica of the patient or other area of plaque mass (typically in injections of about 160 cc each, in several different locations). This is typically performed twice per week, but 48 hours apart, for twelve consecutive weeks. Typically, the carboxy therapy is performed after the low intensity shockwave treatment and the counter-pulsation treatment steps to reduce the dispersal of the carbon dioxide in the injected tissues. U.S. Pat. No. 9,132,245, issued to Mantell, discloses a carboxy therapy application and is incorporated here by reference to disclose one device and method for administering carboxy therapy. The carboxy therapy infuses carbon dioxide into the tissues, causing the body to interpret the presence of the carbon dioxide as an oxygen deficiency, which results in the production of vascular endothelial growth factors (VEGF) in the tissues. This encourages vascular growth and local reduction in fat tissue, which results in increased blood flow to the corpora cavernosa.

An L-type phenylalkylamine class calcium channel blocker, of the type known generically as "Verapamil," is injected into a calcified plaque area of the penile area 118. Typically, in this step 0.625 mg to 2.5 mg of Verapamil is injected into a dorsal tunica of the patient. About 12 Verapamil treatments are administered at a frequency of one every 14 days.

The test battery is repeated 120 to quantify patient treatment progress. If there has not been sufficient improvement over the baseline test, then the treatment steps are repeated 122. Indicia of sufficient improvement include the observance of no plaque in the ultrasound imaging and the observance of a doubling in blood flow in the affected area. Once the desired result is achieved, the patient can return periodically for examination and maintenance treatments 124 if such treatments are indicated.

Alternate embodiments discussed supra for a treatment protocol for Peyronie's disease are illustrated in FIGS. 3-7.

Figure 3:
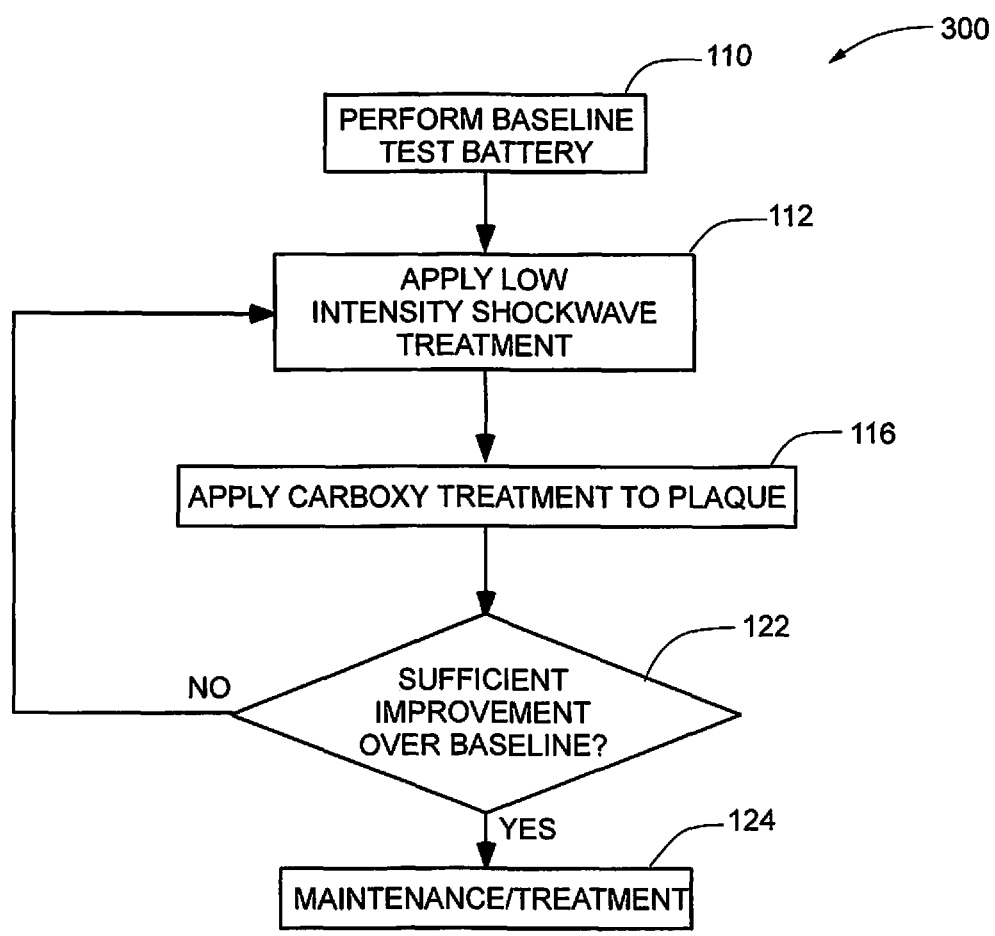
FIG. 3 is a flow chart showing a treatment protocol according to one embodiment of the present invention.

The treatment protocol 300 of FIG. 3 begins with the baseline test battery 110, followed by LISW treatment 112 which is followed by applying the carboxy treatment to the plaque 116, with checking additional test results at 122 to see if results are sufficient. If not, the treatment steps are repeated, beginning with LISW treatment 112 until the test results are sufficiently improved over baseline and maintenance treatments are provided to the patient 124.

Figure 4:
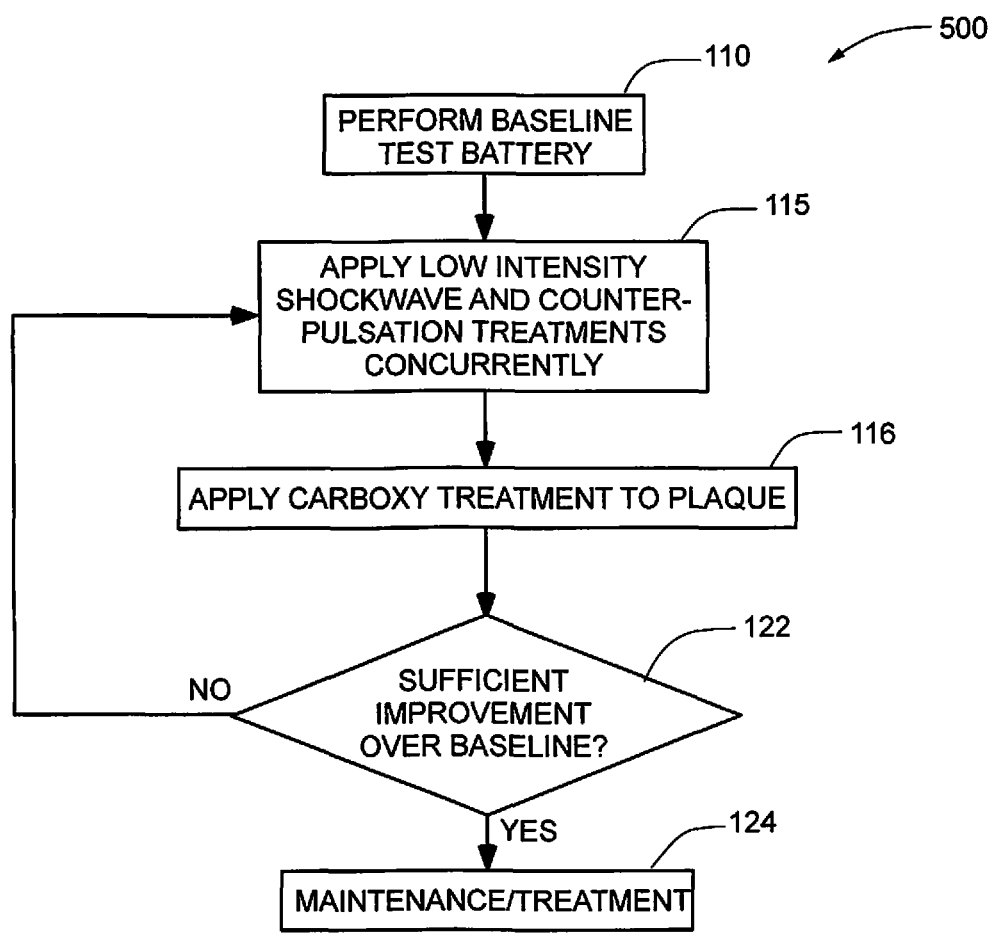
FIG. 4 is a flow chart showing a treatment protocol according to one embodiment of the present invention.

Alternative treatment protocol 500 in FIG. 4 also begins with baseline test battery 100, followed by concurrent treatments of LISW and external counter-pulsation treatments 115. These are followed by applying carboxy treatment 116, with subsequent evaluation of results 122. If insufficient compared with baseline, the steps are repeated beginning with concurrent LISW and counter-pulsation treatments 115 until sufficient test result improvement over baseline is achieved and maintenance treatment protocols are executed 124.

Figure 5:
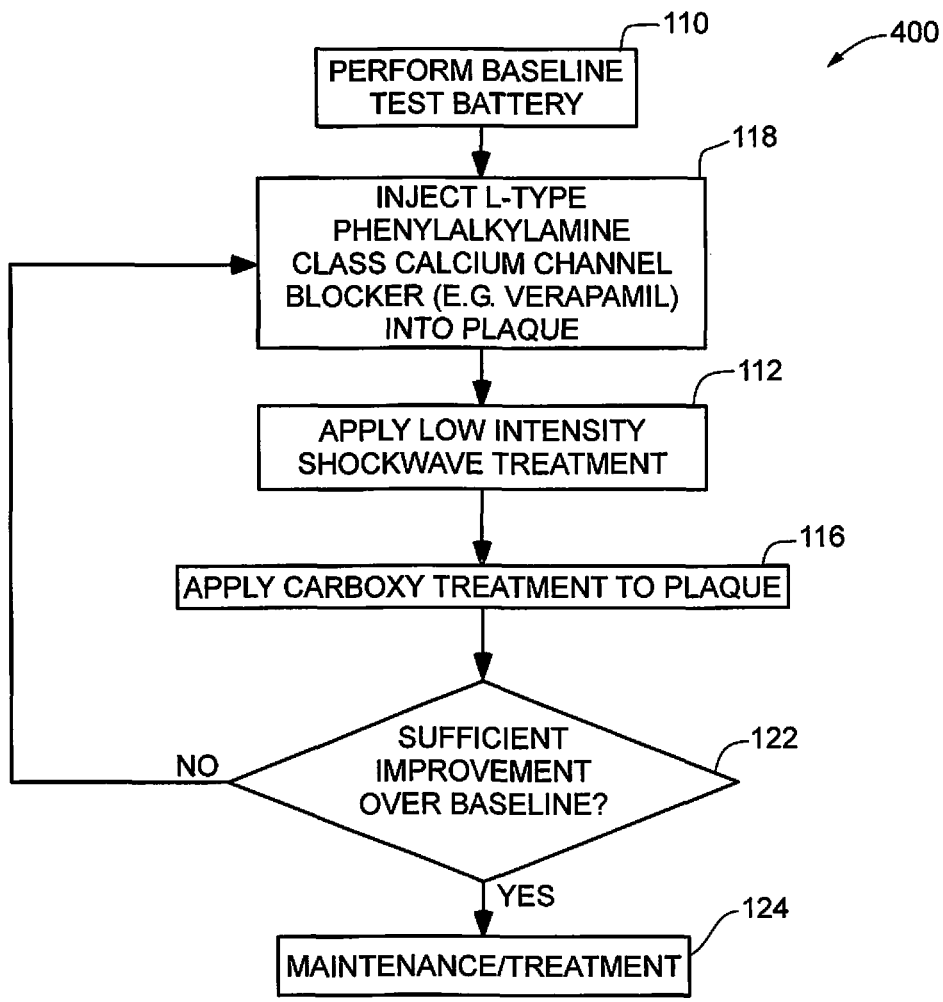
FIG. 5 is a flow chart showing a treatment protocol according to one embodiment of the present invention.

Treatment protocol embodiment 400 of FIG. 5 begins with the baseline test battery 100, followed by injection of the exemplary Verapamil into the plaque 118. This injection is followed by application of LISW treatment 112 which is then followed by application of carboxy treatment to the plaque 116, with subsequent evaluation of results 122. If insufficient compared with baseline, the steps are repeated beginning with injection of the exemplary Verapamil 118 until sufficient test result improvement over baseline is achieved and maintenance treatments 124 are provided to the patient.

The methods of the present invention could also be useful in treating calcification in an individual's hand, or other extremity.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A method of treating a patient having a plaque mass associated with Peyronie's disease in a penile region, comprising the steps of:
    (a) performing a battery of tests to quantify an initial state of parameters associated with Peyronie's disease in the patient;
    (b) applying shock wave treatment to the plaque mass in the penile region, thereby softening the plaque mass and disrupting any calcification in the plaque mass wherein the shock wave treatment comprises a low intensity shock wave treatment having a minimum energy of 0.10 mJmm$^2$;
    (c) applying carboxy treatment comprising injecting carbon dioxide into the plaque mass after the step of applying the shock wave treatment;
    (d) repeating the battery of tests to quantify a current state of parameters associated with Peyronie's disease in the patient and comparing the current state to the initial state; and
    (e) until the current state differs from the initial state by at least a predetermined amount, repeating steps (b) through (d).

2. The method of claim 1, further comprising the step of applying external counter-pulsation treatment to the patient concurrently with the step of applying the shock wave treatment, further softening the plaque mass and disrupting any calcification in the plaque mass.

3. The method of claim 2, wherein the step of applying the external counter-pulsation treatment comprises applying a counter-pulsation treatment about twice per week during a period of at least ten weeks.

4. The method of claim 1, wherein the step of applying shock wave treatment to the plaque mass comprises applying shock wave treatment to the plaque mass for about thirteen treatments over a period of seven to eight weeks, including a two week break period of no shock wave treatment.

5. The method of claim 1, further comprising a step of injecting a therapeutically effective dose of an L-type phenylalkylamine class calcium channel blocker into a calcified plaque area of the penile area either before or after applying shock wave treatment to the plaque mass.

6. The method of claim 5, wherein the L-type phenylalkylamine class calcium channel blocker comprises Verapamil.

7. The method of claim 6, wherein the step of injecting a therapeutically effective dose of Verapamil comprises injecting between 0.625 mg to 2.5 mg of Verapamil into a dorsal tunica of the patient.

8. The method of claim 5, wherein the step of injecting a therapeutically effective dose of an L-type phenylalkylamine class calcium channel blocker comprises performing about 12 treatments at a frequency of every 14 days.

9. The method of claim 1, wherein the step of injecting carbon dioxide into the plaque mass comprises injecting a predetermined amount of carbon dioxide into a dorsal tunica of the patient.

10. The method of claim 1, wherein the step of injecting carbon dioxide into the plaque mass comprises injecting a predetermined amount of carbon dioxide into a corpus cavernosum of the patient.

11. The method of claim 1, wherein the step of injecting carbon dioxide into the plaque mass is performed twice per week, but 48 hours apart, for twelve consecutive weeks.

12. The method of claim 1, wherein the battery of tests includes imaging the plaque with an ultrasound imaging device and the current state differs from the initial state by the predetermined amount when no plaque is observed.

13. The method of claim 1, wherein the battery of tests includes measuring blood flow in penile blood vessels of the patient with a duplex Doppler ultrasonography blood flow device and the current state differs from the initial state by the predetermined amount when about a doubling in blood flow is observed.

14. The method of claim 1, wherein the battery of tests includes measuring pulse wave velocity in a brachial artery and an ankle artery of the patient.

15. A treatment method for a patient having a plaque mass associated with Peyronie's disease in a penile region, comprising the steps of:
    (a) performing a battery of tests to quantify an initial state of parameters associated with Peyronie's disease in the patient;
    (b) applying shock wave treatment to the plaque mass in the penile region, thereby softening the plaque and disrupting calcification in the plaque mass, wherein the shock wave treatment comprises a low intensity shock wave treatment having a minimum energy of 0.10 mJmm$^2$;
    (c) applying a counter pulsation treatment concurrently with the step of applying shock wave treatment to further disrupt calcification in the plaque mass;
    (d) injecting a plurality of doses of 160 cc of carbon dioxide per dose into the plaque mass after the concurrently applied steps of applying shock wave treatment and applying a counter pulsation treatment;
    (e) before the concurrently applied steps of applying shock wave treatment and applying a counter-pulsation treatment, injecting a therapeutically effective dose of Verapamil into a dorsal area of the penile area;
    (f) repeating the battery of tests to quantify a current state of parameters associated with Peyronie's disease in the patient and comparing the current state to the initial state; and
    (g) until the current state differs from the initial state by at least a predetermined amount, repeating steps (b) through (f).

16. The treatment method of claim 15, wherein the step of injecting a therapeutically effective dose of Verapamil comprises the step of injecting between 0.625 mg to 2.5 mg of Verapamil into the dorsal tunica of the patient.

17. The treatment method of claim 15, wherein the step of injecting carbon dioxide into the plaque mass comprises injecting the carbon dioxide into at least one of a dorsal tunica of the patient and a corpus cavernosum of the patient twice per week, but 48 hours apart, for twelve consecutive weeks.

18. The treatment method of claim 15, wherein the battery of tests includes imaging the plaque with an ultrasound imaging device and the current state differs from the initial state by the predetermined amount when no plaque is observed.

19. The treatment method of claim 15, wherein the battery of tests includes measuring blood flow in penile blood vessels of the patient with a duplex Doppler ultrasonography blood flow device and the current state differs from the initial state by the predetermined amount when about a doubling in blood flow is observed.

20. The treatment method of claim 15, wherein the battery of tests includes measuring pulse wave velocity in a brachial artery and an ankle artery of the patient.

\* \* \* \* \*